United States Patent [19]

Kawata

[11] Patent Number: 5,863,772
[45] Date of Patent: Jan. 26, 1999

[54] METHOD OF INDIVIDUAL DISCRIMINATION BY POLYMERASE CHAIN REACTION USING MI PRIMER

[75] Inventor: Motoshige Kawata, Tochigi, Japan

[73] Assignee: Forage Crop Breeding and Seed Research Institute, Tokyo, Japan

[21] Appl. No.: 765,176

[22] PCT Filed: May 10, 1996

[86] PCT No.: PCT/JP96/01246

§ 371 Date: Jan. 13, 1997

§ 102(e) Date: Jan. 13, 1997

[87] PCT Pub. No.: WO96/35807

PCT Pub. Date: Nov. 14, 1996

[30] Foreign Application Priority Data

May 12, 1995 [JP] Japan .................................. 7-138543

[51] Int. Cl.$^6$ ............................. C12P 19/34; C07H 21/04
[52] U.S. Cl. ........................ 435/91.2; 536/22.1; 536/24.3
[58] Field of Search ......................... 435/91.2; 536/24.3, 536/22.1

[56] References Cited

U.S. PATENT DOCUMENTS 5,364,759  11/1994  Caskey et al. ............................... 435/6
5,437,975   8/1995  McClelland et al. ....................... 435/6

OTHER PUBLICATIONS

David et al. Molecular Cloning of a Phosphatidylinositol–anchored Membrane Heparan Sulfate Proteoglycan from Human Lung Fibroblasts, J. Cell Biol., vol. 111(6), pp. 3165–3176, 1990.

Welch et al. Expression of a Glyceraldehyde 3–Phosphate Dehydrogenase Gene Specific to Mouse Spermatogenic Cells, Biol. Repr. vol. 46, pp. 869–878, 1992.

"Discrimination of Epidemic and Sporadic Isolates of *Acinetobacter baumannii* by Repetitive Element PCR–Mediated DNA Fingerprinting", A. C. Reboll, et al., Journal of Clinical Microbiology, vol. 32 No. 11 (1994), pp. 2635–2640.

Applied and Environmental Microbiology, vol. 60 No. 8(1994), M. R. Fries, et al., "Isolation, Characterization, and Distribution of Denitrifying Toluene Degraders from a Variety of Habitats", pp. 2802–2810.

*Primary Examiner*—Kenneth R. Horlick
*Assistant Examiner*—Joyce Tung
*Attorney, Agent, or Firm*—Oblon, Spivak, McClelland, Maier & Neustadt, P.C.

[57] ABSTRACT

A method of discriminating individual organisms which comprises conducting a polymerase chain reaction using DNA fragments of test individuals and a primer having a symmetrical base sequence, separating the amplified DNA fragments by polyacrylamide gel electrophoresis, staining each of the separated DNA fragments by silver staining, and comparing the stained DNA fragments with each other; the above method of discrimination wherein the primer having a symmetrical base sequence is one member selected among the following ones: 5'-CCCTAAAGAAATCCC-3', 5'-TTTAGGGCGGGATTT-3', 5'-AGGGCCTTCCGGGA-3'; and the above method of discrimination wherein the individual organisms are animal or plant individuals. The method of the invention enables individual discrimination to be performed efficiently on the basis of a difference in DNA sequence, because it is possible to clearly ascertain different DNA fragments exhibiting polymorphism among test individuals. It is also possible to clearly ascertain different DNA fragments exhibiting polymorphism among test individuals by appropriately regulating the temperature condition of the polymerase chain reaction. Further it is possible to observe more clearly the DNA fragments exhibiting polymorphism among test individuals.

11 Claims, 5 Drawing Sheets

MI primer used is
(5'-CCCTAAAGAAATCCC-3').

MI primer used is
(5'-TTTAGGGCGGGATTT-3').

MI primer used is
(5'-AGGGCCTTCCGGGA-3').

METHOD OF INDIVIDUAL DISCRIMINATION BY POLYMERASE CHAIN REACTION USING MI PRIMER

This application is a 341 of PCT/JP 06101246, filed May 10, 1996.

TECHNICAL FIELD

The present invention relates to a method of discriminating animal and plant individuals on the basis of a difference in DNA sequence, and more specifically relates to a method enabling individual discrimination by a polymerase chain reaction to be performed more efficiently as compared with a conventional method using a primer prepared on the basis of a known or optional base sequence; it relates to a new method of discriminating individual organisms which comprises conducting a polymerase chain reaction using specific DNA fragments (MI primer) as a primer, separating the amplified DNA fragments by acrylamide gel electrophoresis, staining each of the separated DNA fragments by silver staining, and discriminating the test individuals on the basis of a difference in the amplified DNA fragments.

TECHNICAL BACKGROUND

A method of discriminating animal and plant individuals on the basis of a difference in DNA sequence is internationally important from the standpoint of clarifying the genetic background of test individuals and protecting the rights of breeders and fosterers dealing with the same. As a method of individual discrimination on the basis of a difference in DNA sequence is used a PCR (polymerase chain reaction) method. In order to perform individual discrimination by the PCR method, a base sequence of a primer (short DNA fragments, indispensable for the PCR) is an important factor for the success of the discrimination.

Various primers prepared on the basis of known or optional base sequences have been developed, and methods of individual discrimination by using these known or optional base sequences as a primer for the PCR have been proposed (Skolnick, M. H. and R. B. Wallace, Genomics 2: 273–279 (1988); Williams, J. G. K. et al., Nucleic Acid Res. 18: 6531–6535 (1990)); however, according to conventional methods, it has been often difficult to clearly ascertain different DNA fragments exhibiting polymorphism among test individuals and improvements thereof have been demanded intensely.

In addition, as a method of discriminating test individuals on the basis of a difference in DNA fragments can be mentioned methods proposed in RFLP (Restriction Fragments Length Polymorphysms) (Tangsley, S. D. et al., Biotechnology 7: 257–264 (1989)), the official gazette of Japanese Laid-Open Patent Publication No. 62-500423 (1987) and the official gazette of Japanese Laid-Open Patent Publication No. 6-504427 (1994).

It is guessed that base sequences having a symmetrical structure of a mirror image are scattered among DNAs of organisms. That is, for example, it has been thought generally that the phylogenetic differentiation of plant species occurred along with the change of their genes (DNAs) in the process of evolution of them. It can be guessed by comparing the sequences of genes (DNAs) of different plant species with each other that the DNAs were recombined through domains having common base sequences in the phylogenetic differentiation. The present inventor has engaged in studies about the structural change of DNAs of plant species using rice plant as test materials and has found that when the recombination of DNAs (homologous recombination) is caused through a domain having a common base sequence, the recombinant DNA with a base sequence having a symmetrical structure of a mirror image (mirror image structure) in some cases (Kawata, M. et al., Theor. Appl. Genet. 90: 364–371 (1995)). According to the above, it can be guessed that DNAs of organisms including rice plant, corn and the like contain a base sequence having a symmetrical structure of the mirror image as traces of the recombinations of DNAs caused in the process of evolution of them.

Under these circumstances, taking the above prior arts into consideration, the present inventor has engaged in assiduous studies with a view to developing a primer useful for a method of individual discrimination by the PCR method, and has investigated the efficiency of a base sequence with a symmetrical structure of such a mirror image as a primer, and as a result has found that discrimination of test individuals can be performed efficiently by using a base sequence with said mirror image structure as a primer for the PCR. That is, the present inventor has found that DNA fragments (MI primer) having a symmetrical base sequence with a mirror image structure found by the present inventor enable DNA fragments exhibiting polymorphism among test individuals to be observed more clearly as compared with a primer prepared on the basis of a known or optional base sequence, and that hence the use of the MI primer as a primer for the PCR is effective for individual discrimination, which has led to the accomplishment of the present invention.

SUMMARY OF THE INVENTION

The present invention provides a method of individual discrimination by a polymerase chain reaction using MI primer.

The present invention relates to a method of discriminating individual organisms which comprises conducting a polymerase chain reaction using DNA fragments of test individuals and a primer having a symmetrical base sequence, separating the amplified DNA fragments by acrylamide gel electrophoresis, staining each of the separated DNA fragments by silver staining, and discriminating the test individuals on the basis of a difference in the amplified DNA fragments. Moreover, the present invention relates to the above method of discriminating individual organisms, wherein the primer having a symmetrical base sequence is one member selected among the following ones (SEQ ID NO:1,2,3): 5'-CCCTAAAGAAATCCC-3', 5'-TTTAGGGCGGGATTT-3' and 5'-AGGGCCTTCCGGGA-3'; and it also relates to the above method of discriminating individual organisms, wherein the individual organisms are animal or plant individuals.

The present invention makes it possible to clearly ascertain different DNA fragments exhibiting polymorphism among test individuals, and hence enables individual discrimination to be performed efficiently on the basis of a difference in a DNA sequence. It is also possible to clearly ascertain different DNA fragments exhibiting polymorphism among test individuals by regulating the temperature condition of the PCR. Further, it is possible to observe more clearly DNA fragments exhibiting polymorphism among test individuals as compared with the case of using a primer prepared on the basis of a known or optional base sequence.

DISCLOSURE OF THE INVENTION

It is an object of the present invention to provide a method of discriminating animal and plant individuals on the basis of a difference in DNA sequence.

It is another object of the present invention to provide a new method of individual discrimination by the PCR method which makes it possible to clearly ascertain different DNA fragments exhibiting polymorphism among test individuals by using a specific primer (MI primer)

It is still another object of the present invention to provide a specific primer (MI primer) to be used effectively in the method of individual discrimination by the PCR method.

The present invention for dissolving the above problems is a method of discriminating individual organisms which comprises conducting a polymerase chain reaction using total DNAs of test individuals and a primer having a symmetrical base sequence, separating the amplified DNA fragments by acrylamide gel electrophoresis, staining each of the separated DNA fragments by silver staining, and discriminating the test individuals on the basis of a difference in the amplified DNA fragments.

Moreover, another embodiment of the present invention is the above method of discriminating individual organisms, wherein the primer having a symmetrical base sequence is one member selected among the following ones (SEQ ID NO:1,2,3): (5'-CCCTAAAGAAATCCC-3'), (5'-TTTAGGGCGGGATTT-3') and (5'-AGGGCCTTCCGGGA-3').

Further, still another embodiment of the present invention is the method of discriminating individual organisms as claimed in claim 1, wherein individual organisms are animal or plant individuals.

Subsequently, the present invention will be described in more detail.

The aspect of a method of individual discrimination using MI primer of the present invention will be described hereunder.

As described above, the present invention relates to a method of discriminating DNAs of individual organisms by a polymerase chain reaction which comprises conducting the PCR using total DNAs of test individuals and a primer having a symmetrical base sequence with a mirror image structure (MI primer), separating the amplified DNA fragments by acrylamide gel electrophoresis, staining each of the separated DNA fragments by silver staining, and comparing the stained DNA fragments with each other to discriminate the test individuals on the basis of a difference in the amplified DNA fragments.

In the present invention, as MI primer may be used any one so far as it is a primer comprising DNA fragments having a symmetrical base (nucleotide) sequence with a mirror image structure (mirror image primer, MI primer) and preferable examples thereof include, as shown in FIG. 1 (SEQ ID NO:1,2,3), (5'-CCCTAAAGAAATCCC-3'), (5'-TTTAGGGCGGGATTT-3') and (5'-AGGGCCTTCCGGGA-3') however, it is not restricted to them and those having a symmetrical base sequence with a mirror image structure can be used in the same manner irrespective of a type of them.

As MI primer can be used those with an appropriate structure designed and synthesized by a DNA-synthesizer; besides, it is also possible to use a base sequence with a mirror image structure obtained by screening it in DNAs of organisms and extracting it therefrom.

A PCR solution to be subjected to the PCR can be obtained by using the above MI primer as a primer and preparing a solution containing total DNAs of test individuals, DNA polymerase, four kinds of nucleotides (dATP, dCTP, dGTP, dTTP), potassium ions, magnesium ions, a pH buffer and gelatin according to an ordinary procedure and is not restricted to particular one; for example, as a preferable one can be mentioned a PCR solution comprising 25 ng of total DNAS, 0.5 units of DNA polymerase, 100 $\mu$M of each of four kinds of nucleotides (dATP, dCTP, dGTP, dTTP), 0.05M of KCl as potassium ions, 0.002M of $MgCl_2$ as magnesium ions, 0.01 M of Tris-Cl as a pH buffer and 0.001% of gelatin.

The PCR solution prepared in the above manner is subjected to the PCR, and said PCR can be conducted according to an ordinary procedure using a PCR automatic device such as a DNA Thermal Cycler PJ480 (manufactured by Takara Shuzo, JP). In this case, preferable reaction conditions of the PCR are as below: after a treatment of the PCR solution at 94° C. for 2 minutes, a treatment of it at 94° C. for 2 minutes, at 56° C. for one minute and at 72° C. for one minute is repeated 40 times and finally a treatment of it at 72° C. for 5 minutes is conducted; besides, different DNA fragments can be amplified by regulating the temperature condition of the PCR. The DNA region of the above total DNAs inserted into the primers can be amplified by the above PCR selectively.

The DNA fragments amplified by the PCR are separated by acrylamide gel electrophoresis. As said acrylamide gel electrophoresis can be used preferably migration under the condition of 100 V constant voltage using a gel of 5% acrylamide (mass ratio of acrylamide and BIS acrylamide being 29:1); however, it is not restricted to this migration, and equal or similar ones including agarose gel electrophoresis can be used in the same manner.

After the completion of the operation of the migration by acrylamide electrophoresis, the separated DNAs are stained by silver staining, and then different DNA fragments exhibiting polymorphism among test individuals are ascertained and judged by observing a difference in the migration-graph of the obtained DNA fragments.

The present invention can be utilized as a method of individual discrimination of animals and plants irrespective of the species; it can be preferably used as a method of individual discrimination of organisms, for example, including plants such as rice plant, corn, soybean, wheat, barley and the like, mammals such as bovine, horse, pig and the like, microorganisms such as yeast, lactic acid bacterium and the like, and human and so forth.

An MI primer to be used in the present invention is characterized by its symmetrical base sequence as described above; as will be described in Example later, different DNA fragments exhibiting polymorphism among test individuals can be ascertained clearly by regulating the temperature condition of the PCR. An MI primer according to the present invention enables DNA fragments exhibiting polymorphism among test individuals to be observed more clearly as compared with a conventional primer prepared on the basis of a known base sequence, and it is guessed that the effect of the MI primer is due to a base sequence with a mirror image structure having homology with the base sequence of the MI primer scattered in the DNAs.

BEST EMBODIMENT FOR PERFORMING THE INVENTION

Figure 1:
FIG. 1 shows a primer (MI primer) having a symmetrical base (nucleotide) sequence according to the present invention.
Figure 1:
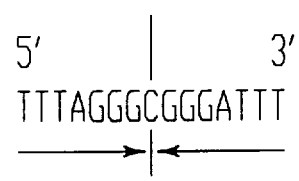
Figure 1:
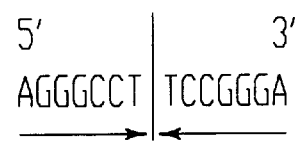

Hereunder the present invention will be described specifically according to Example; however the present invention is not restricted to said Example at all.

EXAMPLE

An example of discrimination of autogamous lines of corn will be shown hereunder.
1) Preparation of Total DNAs
(i) Autogamous Lines of Corn Used
Six kinds of autogamous lines of corn "Na35", "Na42", "H84", "Na30", "Na28" and "Na2" were tested.
(ii) Method of Preparation of DNA Fragments
Preparation of DNAs was performed by using a method partially modified from a method of known report (Murray M. G. and W. F. Thompson, Nucleic Acid Res. 8: 4321–4325 (1980)). Corn seeds were sowed under the dark condition, and buds nipped five days after were frozen with liquid nitrogen and then pulverized; and to the resultant product was added a DNA extraction buffer 1 (0.14M sorbitol, 0.22M Tris-HCl, 0.022M EDTA, 0.8M NaCl, 0.8% CTAB, 1% sodium lauryl sulfate), and the mixture was treated at 65° C. for 30 minutes; then to the mixture was added a DNA extraction buffer 2 (mixed solution of chloroform and isoamyl alcohol of 24:1), and the mixture was shaken for 30 minutes. Subsequently, the resultant product was centrifuged (1,000 g) by a high-speed centrifugal separator for 15 minutes to recover the supernatant DNA solution, and to the obtained supernatant DNA solution were added a DNA extraction buffer 3 (1% CATB, 0.05M Tris-HCl, 0.01M EDTA) and a DNA extraction buffer 4 (10% CATB, 0.8M NaCl), and the resultant product was left to stand for 30 minutes. Thereafter, the product was centrifuged (1,000 g) by a high-speed centrifugal separator for 15 minutes to recover precipitates, and the precipitates were dissolved in a DNA extraction buffer 5 (0.01M Tris-HCl, 0.01M EDTA, 1M NaCl). To the DNA solution were added cesium chloride and ethidium bromide, and the DNA solution was centrifuged (120,000 g) by an ultracentrifugal separator for 8 hour to recover DNA fractions, and the cesium chloride and ethidium bromide were removed to obtain DNAs.

2) Synthesis of MI Primer
(i) Designing for MI Primer
MI primer was designed so as to prepare a base sequence with symmetrical structure, having a boundary site between No. n and No. n+1 in the even-numbered bases (2n), or having an optional middle base of No. n+1 in the odd-numbered bases (2n+1).
(ii) Synthesis of MI Primer by a DNA Synthesizer
Single DNAs were synthesized using a DNA/RNA synthesizer 8905 manufactured by Millipore.

3) Preparation of a PCR Solution
(i) Constitution of a PCR Solution
As a PCR solution was used a solution comprising total DNAs of test individuals, DNA polymerase, four kinds of nucleotides (dATP, dCTP, dGTP, dTTP), potassium ions, magnesium ions, a pH buffer and gelatin, and as a primer was employed the above MI primer.
(ii) Preparation of the PCR Solution
The PCR solution was prepared as a solution comprising 25 ng of total DNAs of test individuals, 0.5 units of DNA polymerase, 100 $\mu$M of each of four kinds of nucleotides (dATP, dCTP, dGTP, dTTP), 0.05M of KCl as potassium ions, 0.002M of $MgCl_2$ as magnesium ions, 0.01M of Tris-HCl as a pH buffer and 0.001% of gelatin.

4) Amplification of DNA Fragments by the PCR
(i) PCR Conditions
PCR conditions are as below: after a treatment of the PCR solution at 94° C. for 2 minutes, a treatment of it at 94° C. for 2 minutes, at 56° C. for one minute and at 72° C. for one minute was repeated 40 times and finally a treatment of it at 72° C. for 5 minutes was conducted.
(ii) PCR by a PCR Automatic Device
The PCR was conducted using a DNA Thermal Cycler PJ480 (manufactured by Takara Shuzo, JP) as a PCR automatic device.

5) Separation of Amplified DNA Fragments by Acrylamide Electrophoresis
i) Conditions and Device of Acrylamide Electrophoresis
Acrylamide electrophoresis was conducted under the condition of 100 V constant voltage using a gel of 5% acrylamide (mass ratio of acrylamide and BIS acrylamide being 29:1). As a migration cell for acrylamide electrophoresis was used a slab gel electrophoresis device with duplex coolers Na-1213 (manufactured by Nippon Eido, JP) and as a power source was used a Cross Power 500 manufactured by ATTO.
(ii) Separation of DNA Fragments (Results of Migration)
DNA fragments with a length of about 1500 base pairs were separated from about 100 base pairs.

6) Staining of the Separated DNA Fragments by Silver Staining
(i) Method and Conditions of Silver Staining
Staining of DNA fragments was performed, using a "Silver Staining II Kit Wako" manufactured by Wako Junyaku, JP; a gel supplied with a migration in 10% trichloroacetic acid was shaken for 10 minutes after the completion of the migration, transferred into a fixative-2 attached to the kit and shaken for 10 minutes, then transferred into a sensitizing solution attached to the kit and shaken for 10 minutes, and further transferred into deionized water and shaken for 10 minutes. Subsequently, the gel was transferred into a staining solution attached to the kit and shaken for 15 minutes, and then transferred into deionized water and shaken for 5 minutes three times. The treated gel was transferred into a developing solution attached to the kit and shaken for 3 minutes, and then transferred into a terminating solution attached to the kit and shaken for 3 minutes to terminate the staining reaction. Finally, the gel was transferred into deionized water and shaken for 2 minutes three times, and then the photographs of the gel was made.

(ii) Results of the Staining of DNA Fragments (FIG. 2 to FIG. 6)

Figure 2:
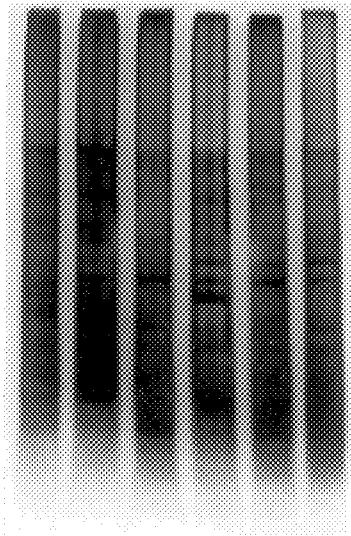
FIG. 2 shows a migration-photo by acrylamide electrophoresis of DNA fragments amplified by the PCR using a primer (5'-GTTGCGATCC-3'-SEQ ID NO:4) prepared on the basis of a base sequence of optional 10 bases according to a conventional method.
Figure 3:
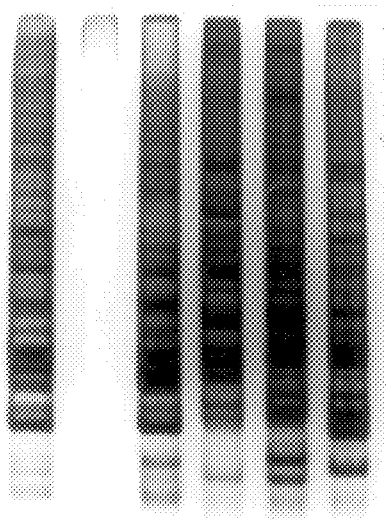
FIG. 3 shows a migration-photo by acrylamide electrophoresis of DNA fragments amplified by the PCR using a primer (5'-GGGGTGGACGGGGC-3'-SEQ ID NO:5) prepared on the basis of a base sequence of optional 14 bases of known human satellite DNAs (lambda 33.3) according to a conventional method.

As a control, the results in the case of using a sequence of optional 10 bases (5'-GTTGCGATCC-3'-SEQ ID NO:4) as a primer are shown in FIG. 2. Polymorphism can be observed among test lines about DNA fragments shown with arrows but is unclear. Besides, the results in the case of using a sequence of 14 bases (5'-GGGGTGGACGGGGC-3'-SEQ ID NO:5) of human satellite DNAs (lambda 33.3) as a primer are shown in FIG. 3. A lot of DNA fragments are amplified by the PCR and discrimination among each line is difficult.

Figure 4:
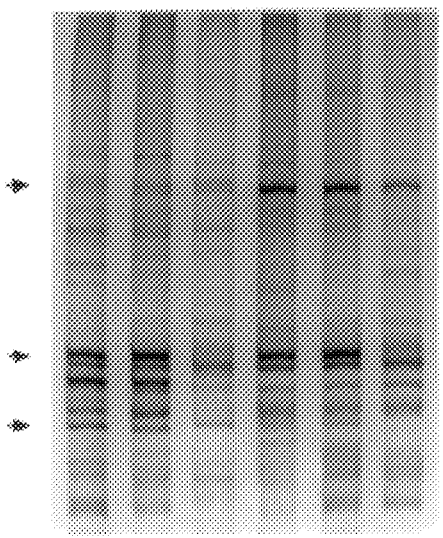
FIG. 4 shows a migration-photo by acrylamide electrophoresis of DNA fragments amplified by the PCR using MI primer of 15 bases (5'-CCCTAAAGAAATCCC-3'-SEQ ID NO:1) according to the present invention.
Figure 5:
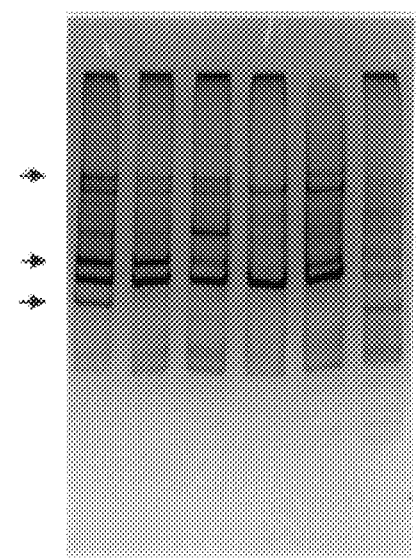
FIG. 5 shows a migration-photo by acrylamide electrophoresis of DNA fragments amplified by the PCR using MI primer of 15 bases (5'- TTTAGGGCGGGATTT-3'-SEQ ID NO:2) according to the present invention.
Figure 6:
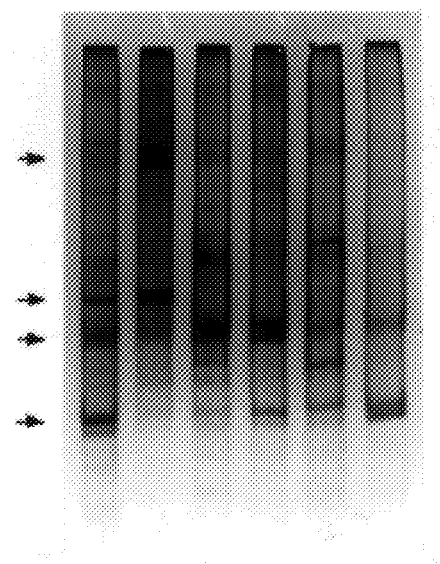
FIG. 6 shows a migration-photo by acrylamide electrophoresis of DNA fragments amplified by the PCR using MI primer of 14 bases (5'-AGGGCCTTCCGGGA-3'-SEQ ID NO:3) according to the present invention.

On the other hand, the results in the cases of using MI primer are shown in FIG. 4 to FIG. 6. The results in the case of using MI primer having a sequence of 15 bases (5'-CCCTAAAGAA ATCCC-3'-SEQ ID NO:1) are shown in FIG. 4. As shown with arrows, polymorphism of DNAs among each line can be observed clearly regarding three kinds of DNA fragments. Besides, the results in the case of using MI primer having a sequence of different 15 bases (5'-TTTAGGGCGGGATTT-3'-SEQ ID NO:2) are shown in FIG. 5. As shown with arrows, polymorphism of DNAs among each line can be observed clearly regarding three kinds of DNA fragments. Similarly, the results in the case of using MI primer having a symmetrical sequence of 14 bases (5'-AGGGCCTTCCGGGA-3'-SEQ ID NO:3) are shown in FIG. 6. As shown with arrows, polymorphism of DNAs among each line can be observed clearly regarding three kinds of DNA fragments.

Figure 7:
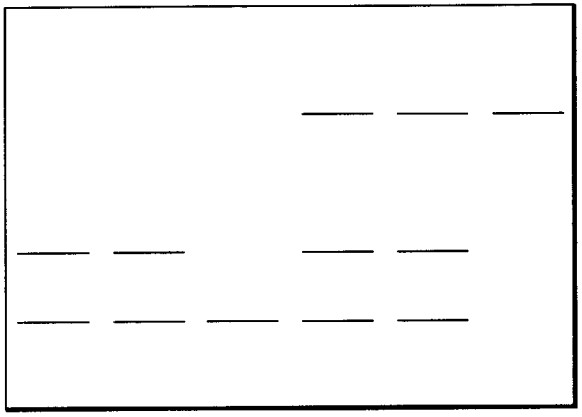
FIG. 7 shows a schematic view of a migration-photo by acrylamide electrophoresis of DNA fragments amplified by the PCR using three kinds of MI primers according to the present invention.
Figure 7:
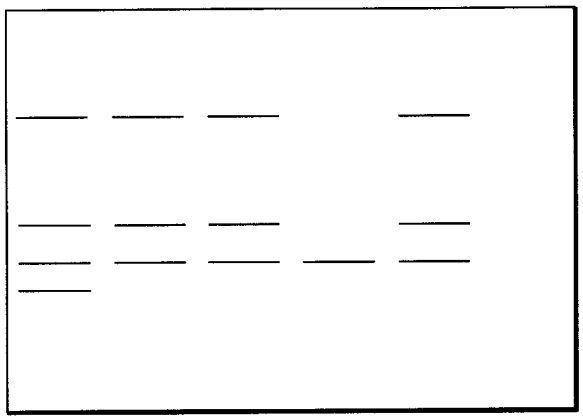
Figure 7:
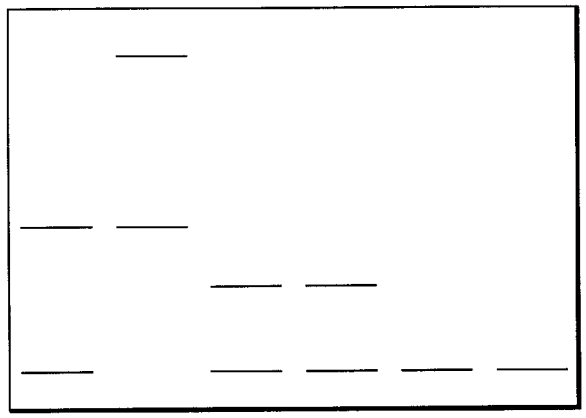

DNA fragments exhibiting polymorphism are summarized schematically in FIG. 7.

7) Discrimination of Test Individuals on the Basis of a Difference in DNA Fragments Amplified by the PCR (i) Method of Discrimination Regarding DNA fragments capable of being observed among test individuals, test individuals were discriminated as the same DNA fragments about those with an equal migration distance and as different DNA fragments about those with a different migration distance.

(ii) Specific Description of the Judgment of Different DNA Fragments Exhibiting Polymorphism of Autogamous Lines of Corn DNA fragments exhibiting polymorphism are summarized schematically in FIG. 7. It has been revealed thereby that DNA fragments exhibiting polymorphism among test individuals can be observed clearly by using MI primer, the use of MI primer as a primer for the PCR is effective for individual discrimination, and that the MI primer enables DNA fragments exhibiting polymorphism among test lines to be observed more clearly as compared with a primer prepared on the basis of a known base sequence or an optional base sequence. According to the results in the cases of using MI primers, specific bar codes (DNA fragments) were recognized about each test line and it has been revealed that it enables individual discrimination of each test line to be performed.

As a result of conducting a test in the same manner using another MI primer, the same results were obtained.

Possibility of Industrial Utilization

As described above in detail, the present invention comprises conducting a polymerase chain reaction using a primer having a symmetrical base sequence with a mirror image structure (MI primer), separating the amplified DNAs by acrylamide gel electrophoresis, staining each of the separated DNA fragments by silver staining, and discriminating the test individuals on the basis of a difference in the amplified DNA fragments; the present invention makes it possible to clearly ascertain different DNA fragments exhibiting polymorphism among test individuals, and hence enables individual discrimination to be performed efficiently on the basis of a difference in a DNA sequence. It is also possible to clearly ascertain different DNA fragments exhibiting polymorphism among test individuals by regulating the temperature condition of the PCR. Further, it is possible to observe more clearly the DNA fragment exhibiting polymorphism among test individuals as compared with the case of using a primer prepared on the basis of a known base sequence or an optional base sequence.

What is claimed is:

1. A method of discriminating individual organisms which comprises conducting a polymerase chain reaction using DNA fragments of test individuals and a primer to produce amplified DNA fragments, separating the amplified DNA fragments by acrylamide gel electrophoresis to produce separated DNA fragments, staining each of the separated DNA fragments by silver staining, and discriminating the test individuals on the basis of a difference in the amplified DNA fragments,
wherein
the base sequence of said primer has mirror symmetry about the center of said base sequence, and
said center of said base sequence is either (1) between base n and base n+1 when the number of bases in said primer, 2n, is an even number or (2) at base n+1 when the number of bases in said primer. 2n+1, is an odd number.

2. The method of discriminating individual organisms as claimed in claim 1, wherein said primer is selected from the group consisting of (5'-CCCTAAAGAAATCCC-3') (SEQ ID NO: 1), (5'-TTTAGGGCGGGATTT-3') (SEQ ID NO: 2) and (5'-AGGGCCTTCCGGGA-3') (SEQ ID NO. 3).

3. The method of discriminating individual organisms as claimed in claim 1, wherein the individual organisms are animal or plant individuals.

4. An oligonucleotide primer selected from the group consisting of 5'-CCCTAAAGAAATCCC-3' (SEQ ID NO: 1), 5'-TTTAGGGCGGGATTT-3'(SEQ ID NO: 2) and 5'-AGGGCCTTCCGGGA-3'(SEQ ID NO: 3).

5. The primer of claim 4, which is 5'-CCCTAAAGAAATCCC-3'(SEQ ID NO: 1).

6. The primer of claim 4, which is 5'-TTTAGGGCGGGATTT-3'(SEQ ID NO: 2).

7. The primer of claim 4, which is 5'-AGGGCCTTCCGGGA-3'(SEQ ID NO: 3).

8. In a method of discriminating individual organisms which comprises conducting a polymerase chain reaction using DNA fragments of test individuals and a primer to produce amplified DNA fragments, separating the amplified DNA fragments to produce separated DNA fragments, detecting the separated DNA fragments, and discriminating the test individuals on the basis of a difference in the amplified DNA fragments, the improvement comprising:

using as said primer an oligonucleotide having a base sequence which has mirror symmetry about the center of said base sequence, and said center of said base sequence is either (1) between base n and base n+1 when the number of bases in said primer, 2n, is an even number or (2) at base n+1 when the number of bases in said primer, 2n+1, is an odd number.

9. The method of claim 8, wherein said primer is 5'-CCCTAAAGAAATCCC-3'(SEQ ID NO: 1).

10. The method of claim 8, wherein said primer is 5'-TTTAGGGCGGGATTT-3'(SEQ ID NO: 2).

11. The method of claim 8, wherein said primer is 5'-AGGGCCTTCCGGGA-3'(SEQ ID NO: 3).

\* \* \* \* \*

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: cDNA to mRNA ( x i ) SEQUENCE DESCRIPTION: SEQ ID NO:1:

C C C T A A A G A A  A T C C C        1 5

( 2 ) INFORMATION FOR SEQ ID NO:2:

( i ) SEQUENCE CHARACTERISTICS:
        ( A ) LENGTH: 15 base pairs
        ( B ) TYPE: nucleic acid -continued

```
        ( C ) STRANDEDNESS: single
        ( D ) TOPOLOGY: linear ( i i ) MOLECULE TYPE: cDNA to mRNA ( x i ) SEQUENCE DESCRIPTION: SEQ ID NO:2:

T T T A G G G C G G   G A T T T                                                       15

( 2 ) INFORMATION FOR SEQ ID NO:3:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i i ) MOLECULE TYPE: cDNA to mRNA ( x i ) SEQUENCE DESCRIPTION: SEQ ID NO:3:

A G G G C C T T C C   G G G A                                                         14

( 2 ) INFORMATION FOR SEQ ID NO:4:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "PRIMER"

( x i ) SEQUENCE DESCRIPTION: SEQ ID NO:4:

G T T G C G A T C C                                                                   10

( 2 ) INFORMATION FOR SEQ ID NO:5:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "PRIMER"

( x i ) SEQUENCE DESCRIPTION: SEQ ID NO:5:

G G G G T G G A C G   G G G C                                                         14
```